United States Patent
Colomb et al.

(10) Patent No.: US 10,342,937 B2
(45) Date of Patent: Jul. 9, 2019

(54) FLUID-PRODUCT DISTRIBUTION DEVICE

(71) Applicant: APTAR FRANCE SAS, Le Neubourg (FR)

(72) Inventors: Arnaud Colomb, Verneuil sur Seine (FR); Maxime Kirniak, Rouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 707 days.

(21) Appl. No.: 14/778,119

(22) PCT Filed: Mar. 18, 2014

(86) PCT No.: PCT/FR2014/050619
§ 371 (c)(1),
(2) Date: Sep. 18, 2015

(87) PCT Pub. No.: WO2014/147330
PCT Pub. Date: Sep. 25, 2014

(65) Prior Publication Data
US 2016/0287818 A1   Oct. 6, 2016

(30) Foreign Application Priority Data
Mar. 19, 2013   (FR) ...................................... 13 52423

(51) Int. Cl.
*A61M 15/00* (2006.01)

(52) U.S. Cl.
CPC ...... *A61M 15/0051* (2014.02); *A61M 15/004* (2014.02); *A61M 15/0026* (2014.02);
(Continued)

(58) Field of Classification Search
CPC .......... A61M 15/0026; A61M 15/0036; A61M 15/004; A61M 15/0051; A61M 15/0055; A61M 15/0008; A61M 15/0091
See application file for complete search history.

(56) References Cited

U.S. PATENT DOCUMENTS 7,434,579 B2 * 10/2008 Young ............... A61M 15/0045
128/203.15
2002/0053344 A1   5/2002 Davies et al.
(Continued)

FOREIGN PATENT DOCUMENTS

FR   2 881 117 A1   7/2006
FR   2 924 352 A1   6/2009
(Continued)

OTHER PUBLICATIONS

International Search Report for PCT/FR2014/050619 dated Jun. 6, 2014 [PCT/ISA/210].
(Continued)

*Primary Examiner* — Timothy A Stanis
(74) *Attorney, Agent, or Firm* — Sughrue Mion, PLLC

(57) ABSTRACT

A fluid dispenser device including a body and a cover that pivots between a closed position and an open position and reservoirs each containing a dose of fluid. The reservoirs are arranged on a strip and an opening mechanism is provided. The device includes a movable support to move a reservoir against the opening mechanism. The movable support is movable between a non-dispensing position and a dispensing position. The device includes a strip-rolling system having a drum and an actuator member. The actuator member turning relative to the body in a first direction when the movable support is moved from the non-dispensing position towards the dispensing position, and in a second direction when the movable support is moved from their dispensing position towards the non-dispensing position. The actuator member causes the drum to turn only when turning in the second turning direction.

13 Claims, 4 Drawing Sheets

(52) U.S. Cl.
CPC .... *A61M 15/0036* (2014.02); *A61M 15/0055* (2014.02); *A61M 15/0091* (2013.01); *A61M 15/0008* (2014.02); A61M 15/0068 (2014.02); A61M 2202/064 (2013.01)

(56) References Cited

U.S. PATENT DOCUMENTS

| | | |
|---|---|---|
| 2008/0099015 A1 | 5/2008 | Pocock et al. |
| 2010/0307493 A1 | 12/2010 | Kirniak |
| 2011/0036349 A1 | 2/2011 | Colomb et al. |
| 2015/0209531 A1* | 7/2015 | Meliniotis ......... A61M 15/0045 128/203.15 |

FOREIGN PATENT DOCUMENTS

| | | |
|---|---|---|
| WO | 2006/079750 A1 | 8/2006 |
| WO | 2008/012458 A2 | 1/2008 |
| WO | 2009/007640 A1 | 1/2009 |
| WO | 2009/077700 A2 | 6/2009 |
| WO | 2009/136098 A2 | 11/2009 |
| WO | 2011/154658 A1 | 12/2011 |
| WO | 2011/154659 A1 | 12/2011 |

OTHER PUBLICATIONS

International Preliminary Report on Patentability dated Oct. 1, 2015 issued by the International Searching Authority in counterpart International Application No. PCT/FR2014/050619.

* cited by examiner

FLUID-PRODUCT DISTRIBUTION DEVICE

CROSS REFERENCE TO RELATED APPLICATIONS

This application is a National Stage of International Application No. PCT/FR2014/050619, filed on Mar. 18, 2014, which claims priority from French Patent Application No. 1352423, filed on Mar. 19, 2013, the contents of all of which are incorporated herein by reference in their entirety.

The present invention relates to a fluid dispenser device, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in placing the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally initially loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the preceding dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. Another problem that may occur relates to assembling certain parts, in particular movable parts, that need to withstand large stresses in operation, and for which assembly needs to be particularly reliable so as to avoid any risk of malfunctioning. With the small size of certain parts, it can be complicated to guarantee such reliable assembly. With inhalers that are primed, e.g. while opening, then triggered by inhalation, it is important to avoid or to limit the risks of accidental triggering after priming and before inhalation, without imposing a triggering inhalation threshold that is too high, which could be difficult for weak people to achieve. Another problem that exists with inhalers provided with blister strips is associated with moving the strip, and with storing the used portion of the strip. Thus, depending on the length of the strip, a large space can turn out to be necessary, and any blockage of the blister strip can prevent the inhaler from functioning properly. In addition, when the device for advancing the strip pulls simultaneously on the leading end of the strip so as to avoid poor rolling up, a problem can occur over successive actuations, in particular because the rolled-up diameter of the used strip increases progressively.

An object of the present invention is to provide a fluid dispenser device, in particular a dry-powder inhaler, that does not have the above-mentioned drawbacks.

In particular, an object of the present invention is to provide such a device that is simple and inexpensive to manufacture and to assemble, that can be assembled and used reliably, guaranteeing metering accuracy and reproducibility on each actuation, providing an optimum yield with regard to the effectiveness of the treatment, by making it possible to dispense a substantial fraction of the dose to the zones to be treated, in particular the lungs, while avoiding, in safe and effective manner, any risk of overdosing, and that is as compact as possible, while guaranteeing sealing and absolute integrity of all of the doses up to their expulsion.

The present invention thus provides a fluid dispenser device including a body and at least one cover element that is mounted to pivot on said body between a closed position and an open position, said device including a plurality of individual reservoirs each containing a single dose of fluid, such as powder, said individual reservoirs being arranged on an elongate strip, opening means being provided for opening an individual reservoir each time the device is actuated, said device including movable support means that are adapted to move an individual reservoir against said opening means on each actuation, said movable support means being movable between a non-dispensing position and a dispensing position, the device including a strip-rolling system comprising a drum and an actuator member, the leading end of said elongate strip being fastened to said drum, and said actuator member turning relative to the body in a first turning direction when said movable support means are moved from their non-dispensing position towards their dispensing position, and in a second turning direction, opposite to said first turning direction, when said movable support means are moved from their dispensing position towards their non-dispensing position, said actuator member causing said drum to turn only when turning in said second turning direction.

Advantageously, said drum is prevented from turning in said first turning direction by non-return means.

Advantageously, said non-return means comprise a lug that is arranged on a deformable tab, said lug co-operating with a first set of teeth of said drum so as to prevent said drum from turning in said first turning direction, said deformable tab deforming so as to enable said drum to turn in said second turning direction.

Advantageously, said actuator member includes a flexible tab, said flexible tab co-operating with a second set of teeth of said drum so as to turn said drum in said second turning direction, said flexible tab deforming so as to enable said actuator member to turn relative to said drum in said first turning direction.

Advantageously, said actuator member includes a rigid finger that co-operates with a control opening in said movable support means.

Advantageously, the device includes an inhalation trigger system that comprises a deformable air chamber that co-operates with an inhalation piece, and a trigger element that co-operates with said air chamber, such that during inhalation through said inhalation piece, said air chamber is deformed and said trigger element actuates said opening means, such that during inhalation through the inhalation piece, a reservoir is opened by said opening means.

Advantageously, said opening means include a perforator element that is stationary relative to said main body and that is adapted to cut a closure wall of the reservoir in such a manner that the cut portion(s) does/do not obstruct the opening(s) that is/are formed.

These characteristics and advantages and others of the present invention appear more clearly from the following detailed description, given by way of non-limiting example, and with reference to the accompanying drawing, and in which.

Figure 1:
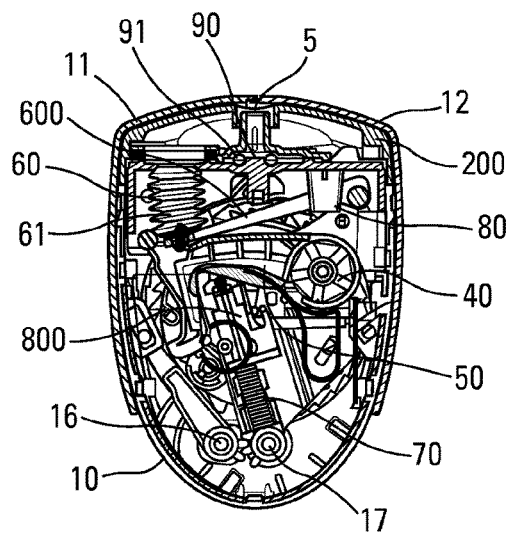
FIG. 1 is a diagrammatic section view of a dispenser device in an advantageous embodiment, in the closed position of the covers, showing some elements of the dispenser device.
Figure 2:
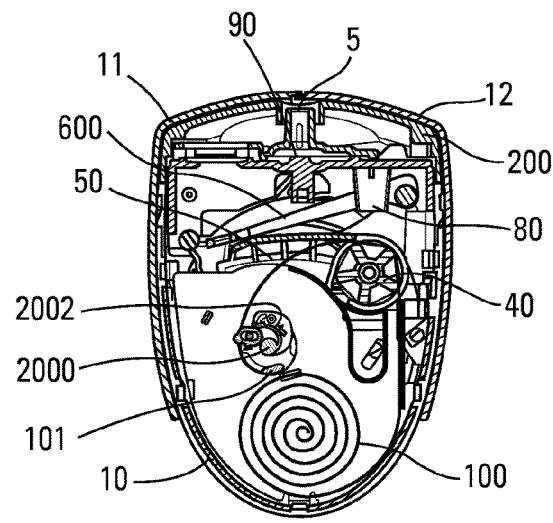
FIG. 2 is a view similar to the view in FIG. 1, showing other elements of the dispenser device.
Figure 3:
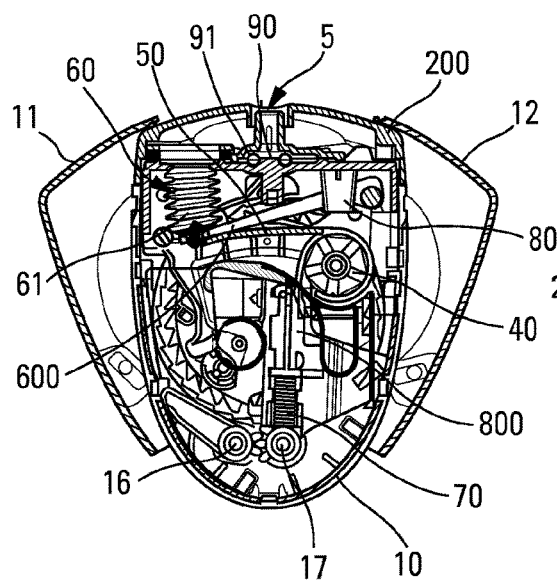
FIG. 3 is a view similar to the view in FIG. 1, but in the open position of the covers, before inhalation.
Figure 4:
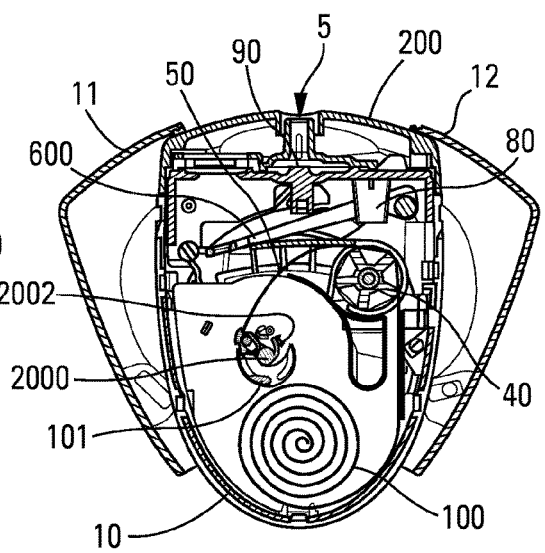
FIG. 4 is a view similar to the view in FIG. 2, but in the open position of the covers, before inhalation.
Figure 5:
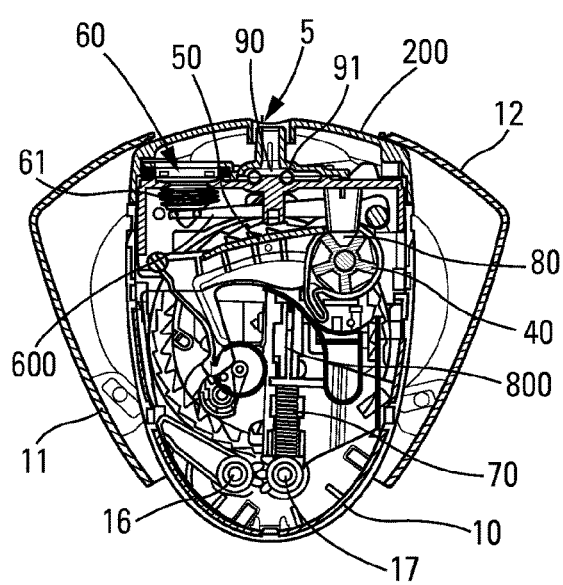
FIG. 5 is a view similar to the view in FIG. 1, but in the open position of the covers, after inhalation.
Figure 6:
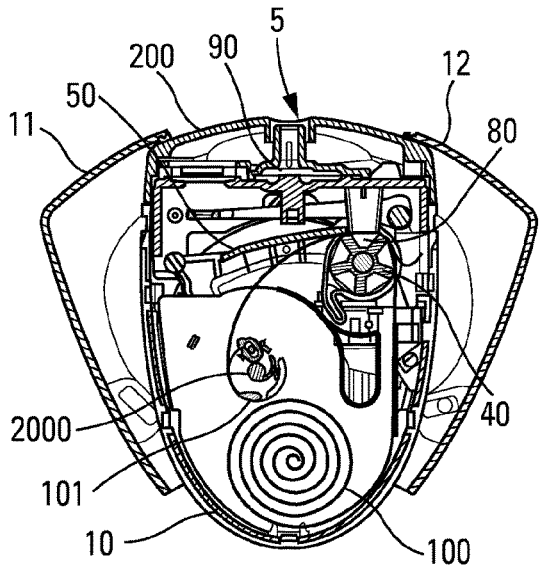
FIG. 6 is a view similar to the view in FIG. 2, but in the open position of the covers, after inhalation.
Figure 7:
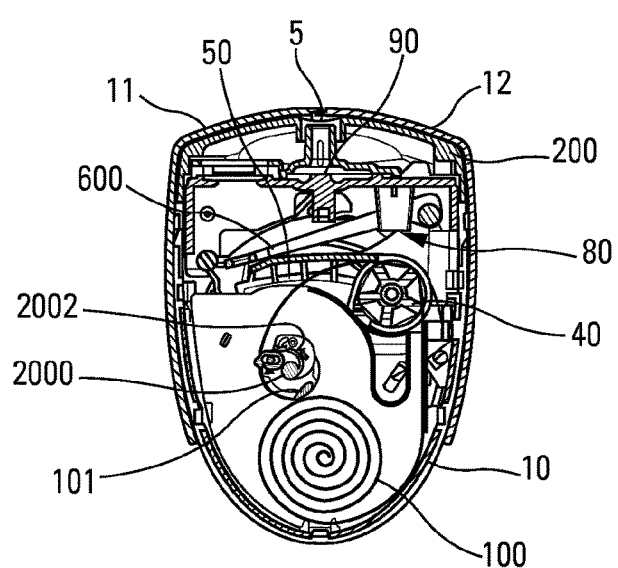
FIG. 7 is a view similar to the view in FIG. 2, in the closed position of the covers.
Figure 8:
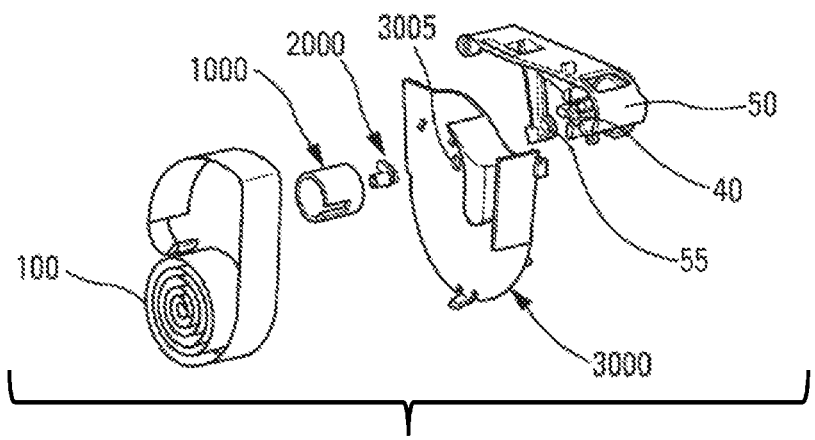
FIG. 8 is an exploded diagrammatic perspective view of a strip-rolling system in an advantageous variant.
Figures 9, 10, 11:
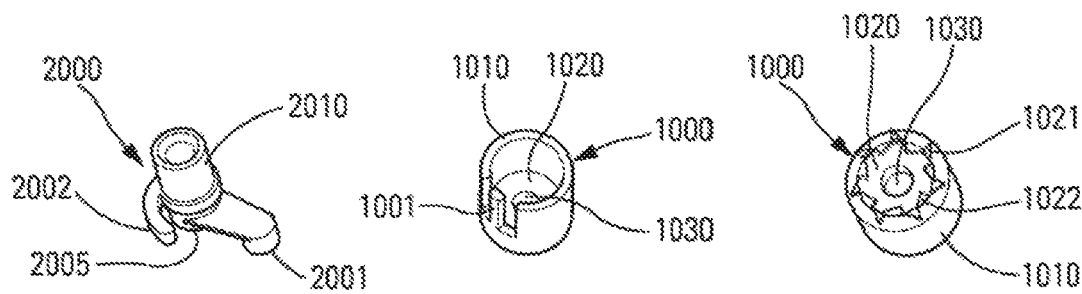
FIG. 9 is a diagrammatic perspective view of the actuator member in an advantageous variant.
FIG. 10 is a diagrammatic plan view in perspective of the drum in an advantageous variant.
FIG. 11 is a diagrammatic plan view in perspective of the drum in an advantageous variant.
Figure 12:
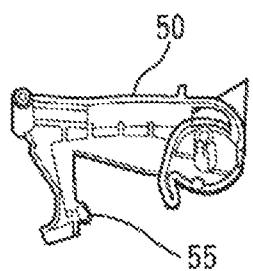
FIG. 12 is a diagrammatic perspective view of the movable support means in an advantageous variant.
Figure 13:
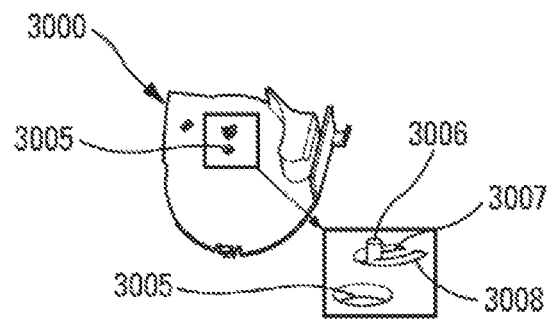
FIG. 13 is a larger-scale diagrammatic detail view in perspective of the support plate in an advantageous variant.

FIGS. 1 to 7 show an advantageous embodiment of a dry-powder inhaler. For the purpose of clarity, not all of the elements of the device are visible in all of the figures. The inhaler includes a main body 10 on which there can be slidably mounted two cover-forming portions 11, 12 that are adapted to be opened so as to open and prime the device. The main body 10 can be approximately rounded in shape, as shown in the figures, but it could be of any other appropriate shape. A mouthpiece 200 is assembled on said body 10. The mouthpiece 200 defines a dispenser orifice 5 through which the user inhales while the device is being actuated. The dispenser orifice 5 is typically arranged approximately in the center of the mouthpiece 200. The covers 11, 12 can open by pivoting about a common pivot axis, or about two parallel axes by being meshed together. Any other means for opening the device can be envisaged. In a variant, the device could include only a single cover instead of two.

Inside the main body 10 an elongate strip 100 of individual reservoirs is provided. The elongate strip 100 is visible in FIGS. 2, 4, 6, 7, and 8. The individual reservoirs, also referred to as blisters, are not shown in the figures for the purpose of clarity. The blisters are disposed one behind another, in manner known per se. The blister strip 100 is advantageously constituted by a base layer or wall that forms the cavities receiving the doses of powder, and by a closure layer or wall that covers each of said blisters in sealed manner. Before first use, the blister strip 100 can be rolled-up inside the main body 10, preferably in a storage portion, and strip mover means 40, in particular rotary means, are provided for progressively unrolling the blister strip 100 and for causing it to advance.

The strip portion including the empty blisters is advantageously adapted to be rolled-up at another location of said body 10, preferably a reception portion, as described in greater detail below.

The inhaler includes blister opening means 80 (shown only very diagrammatically for the sake of clarity) preferably comprising a perforator and/or cutter needle for perforating and/or cutting the closure layer of the blisters. Preferably, the opening means comprise a perforator element 80 that is stationary relative to the body 10, and against which a respective blister is moved on each actuation by movable support means 50. The movable support means 50, in particular means that are mounted to pivot on the main body 10, are provided for bringing a respective blister into a dispensing position each time the device is actuated. The movable support means 50 are mounted to pivot between a non-dispensing position and a dispensing position in which a blister co-operates with said opening means. The blister is thus perforated by said perforator element that penetrates into said blister so as to expel the powder by means of the user inhaling. Advantageously, the perforator element is adapted to cut a closure wall of the reservoir in such a manner that the cut portion(s) does/do not obstruct the opening(s) that is/are formed. Documents WO 2006/079750 and WO 2009/007640 describe such blister opening means, and they are thus incorporated in the present description by way of reference.

The mover means 40 are adapted to cause the blister strip to advance after each inhalation of the user. The movable support means 50 are adapted to move the blister to be emptied against said opening means 80 during actuation, before each inhalation. The movable support means can be urged by a resilient element 70, such as a spring or any other equivalent resilient element, said resilient element being suitable for being prestressed while the device is being opened.

Preferably, the mover means 40 are formed by an indexer wheel that receives and guides the blister strip. The description below is thus made with reference to such an indexer wheel 40. Turning the indexer wheel 40 causes the blister strip to advance. Before each inhalation, a full blister is always in a position facing the opening means 80. The movable support means 50 can include a pivot member that is mounted to pivot about a pivot axis, said indexer wheel 40 advantageously being rotatably mounted on said pivot member.

An actuation cycle of the device can be as follows. During opening of the device, the two cover-forming lateral portions 11, 12 are moved away from each other by pivoting about the body so as to open the device and thus spring-load the device. In this position, the indexer wheel 40 cannot be moved towards the perforator element 80, since the movable support means 50 are held by appropriate blocking means (not shown for the sake of clarity). Documents WO 2009/077700 and WO 2009/136098 describe such blocking means, and they are thus incorporated in the present description by way of reference. While the user is inhaling through the mouthpiece, the blocking means are unblocked, thereby causing the movable support means 50 to pivot and said indexer wheel 40 to move towards the needle, and thereby causing a blister to be opened.

As explained above, it is desirable for the opening means to be actuated by the user inhaling. In order to trigger the opening means by inhalation, an inhalation trigger system 60 is provided that advantageously comprises an air chamber 61 that is deformable under the effect of inhalation, the air chamber being adapted to release the blocking means. The air chamber 61 may advantageously be made in the form of a bellows. Inhalation by the user causes said deformable air-chamber to deform, thus releasing said blocking means and therefore enabling the movable support means to be moved, and therefore enabling a respective blister to be moved towards its opening position. The blister is therefore opened only on inhalation, such that it is emptied simultaneously. Thus, there is no risk of any of the dose being lost between opening the blister and emptying it.

The inhaler in FIGS. 1 to 7 further includes a dispersion chamber 90 for receiving the dose of powder after a respective blister has been opened. The dispersion chamber is advantageously provided with at least one and preferably more beads 91 that are moved inside said chamber 90 during inhalation, in particular so as to improve dispensing of the air and powder mixture after a blister has been opened, in order to increase the effectiveness of the device.

After inhalation, when the user closes the device, all of the components return to their initial, rest positions. The device is thus ready for a new utilization cycle.

In an advantageous aspect of the inhaler, the blisters are formed on a flexible elongate strip that, initially, is mainly stored in the form of a roll in a storage housing inside the main body 10 of the device. Advantageously, the rolled-up blister strip is held by inner walls of said storage housing without its rear end (rear in the direction of advance of the blister strip) being fastened relative to said main body 10, thereby enabling the blister-strip roll to be assembled more easily inside the device. The blister strip is moved by means of the indexer wheel 40 that advantageously presents at least one and preferably more recesses, each having a shape that corresponds to the shape of the blisters. Thus, when the indexer wheel 40 turns, it causes the blister strip to advance. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of sprocket wheels co-operating with said holes.

After opening one or more blisters, the blister-strip portion with the empty blisters, i.e. the leading portion of said strip 100, must be suitable for being stored in easy and compact manner in the device, while avoiding any risk of blockage. Advantageously, the used blister strip is rolled-up automatically, once again forming a roll.

In still another aspect of the inhaler, a dose counter or indicator device (not shown for the sake of clarity) may also be provided. The device may include numbers or symbols that are marked directly on the blister strip, and that are visible through an appropriate window in the main body 10 of the device. In a variant, it is possible to envisage using a counter with one or more rotary disks or rings including numbers or symbols. Documents WO 2008/012458 and WO 2011/154659 describe such counters. An object of the invention is to avoid counting doses that have not been dispensed, e.g. in the event of a manipulation error, or of an incomplete manipulation of the device. It is thus desirable that the counter or indicator is actuated only once the user has inhaled, since it is this inhalation that makes it possible for the blister to open and the dose contained therein to be dispensed. Advantageously, the counter is thus actuated after inhalation, when the user closes the device.

One of the cover elements, e.g. the movable cover element 12, is secured to a cocking member 800 that can slide in an appropriate housing. The cocking member 800 thus advantageously pivots relative to said body 10 together with the cover element 12. The cocking member 800 may be moved against the spring 70, advantageously a coil spring. The cocking member 800 is thus connected at one end to said spring 70, and at the other end it co-operates with the movable support means 50, in particular with a pivot member that is mounted to pivot on the body 10, and on which the indexer wheel 40 is fastened in rotary manner.

When the movable cover element 12 is opened, the cocking member 800 is moved, compressing the spring 70. The pivot member of the movable support means 50 is itself prevented from moving by the above-mentioned blocking means that are released only at the moment of inhalation. Thus, in the absence of any inhalation in the open position, closing the cover elements 11, 12 would merely cause the cocking member 800 to return to its rest position and the spring 70 to decompress.

Thus, by opening the inhaler, the user primes the system. If the user does not inhale and closes the inhaler, said inhaler merely returns to its start position without moving the blister strip or the blocking means. There is thus no risk of a blister (and thus an active dose of substance) being lost by accidental or incomplete actuation in which the user does not inhale between opening and closing. Opening the blister, emptying it, dispensing the powder into the lungs of the user, moving the blister strip to bring a new full blister to face the opening means, and counting the dose are thus possible only if the user inhales.

The blocking means that, before inhalation, block the movable support means 50 and in particular the pivot member that co-operates with the cocking member, are connected to the deformable air chamber 61 that is sensitive to the user inhaling, by means of a trigger element 600, so that while the user is inhaling, said deformable air chamber deforms, causing the trigger element 600 to pivot and thus causing said blocking means to be released. This enables said movable support means 50 to be moved towards their dispensing position under the effect of the force exerted by the compressed spring 70 on the cocking member 800 that pushes against the pivot member 50. Such movement causes a full blister to be opened and a dose to be dispensed.

A cam surface is formed on said movable support means 50, on which the cocking member 800 slides. The cocking member 800 is thus adapted to compress the spring 70 when the cover element 12 is open, and to decompress said spring 70 when said cover element 12 is closed. Advantageously, in its portion in contact with the cam surface, the cocking member 800 includes a rounded portion for facilitating sliding of the cocking member 800 on said cam surface.

After inhalation, i.e. in the dispensing position, the blocking means have been released, and the movable support means 50 have been moved upwards by the compressed spring 70.

Advantageously, the two movable cover elements 11, 12 mesh together via appropriate gearing so as to guarantee symmetrical opening and closing of said two movable cover elements. They can mesh together in the proximity of their pivot axes 16, 17.

In the invention, a strip-rolling system is provided for ensuring correct rolling of the strip portion including the empty blisters, i.e. the leading portion in the direction of advance of the blister strip in the device.

FIGS. 8 to 13 show various components in an advantageous variant of said rolling system. In this variant, the leading end 101 of the blister strip 100, in the direction of advance of said strip 100, is fastened to a rotary drum 1000, in particular on a finger 1001 of said drum 1000. Said drum comprises a hollow sleeve 1010 having one axial end that is closed by an axial wall 1020 that is provided with a central opening 1030.

Advantageously, the finger 1001 is formed in said sleeve 1010. On its outer face, the axial wall 1020 includes first and second sets of teeth 1021 and 1022, said sets of teeth projecting axially out from said axial wall 1020.

An actuator member 2000 is arranged in concentric or coaxial manner against said outer face of said axial wall 1020 of the drum 1000. The actuator member 2000 includes a first axial lug 2010 that passes through said central opening 1030 of the drum so as to extend axially inside said sleeve 1010 of said drum 1000. At its opposite axial end, said actuator member 2000 includes a second axial lug 2005 that co-operates with an opening 3005 that is formed in a support plate 3000 that is secured to the body 10. Said second axial lug 2005 of said actuator member 2000 is rotatably mounted in said opening 3005. Said actuator member 2000 includes a rigid finger 2001 that is adapted to co-operate with a control opening 55 of said movable support means 50. The actuator member 2000 also includes a flexible tab 2002 that is adapted to co-operate with said second set of teeth 1022 of said drum 1000. Said actuator member 2000 turns relative to the body 10 in a first turning direction when said movable support means 50 are moved from their non-dispensing position towards their dispensing position, and in a second turning direction, opposite to said first turning direction, when said movable support means 50 are moved from their dispensing position towards their non-dispensing position.

The support plate 3000 includes a projecting lug 3006 that is formed on a deformable tab 3007 that is defined by a U-shaped cutout 3008 in said support plate 3000. The lug 3006 is adapted to co-operate with said first set of teeth 1021 of the drum 1000.

The operation of the strip-rolling system is described with reference to FIGS. 14 to 17.

Figure 14:
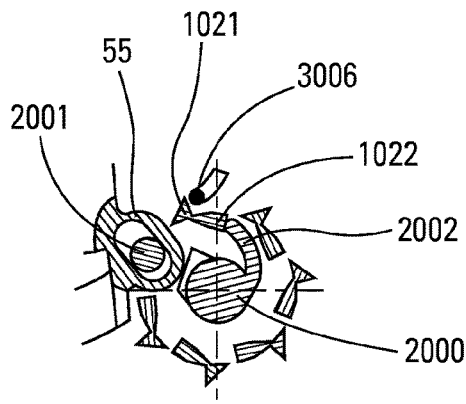
FIGS. 14 to 17 are diagrammatic section views of the strip-rolling system, respectively before inhalation, during inhalation, after inhalation, and while returning to the start position.

FIG. 14 shows the rest position prior to actuation.

Figure 15:
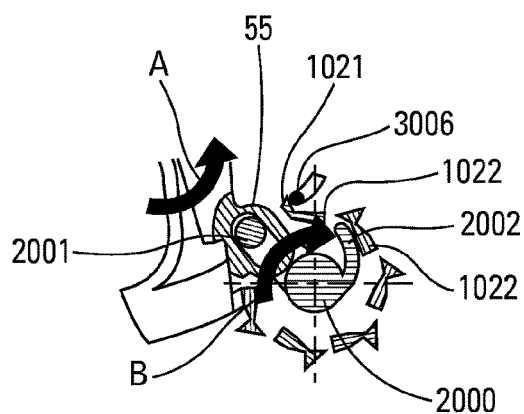
Figure 16:
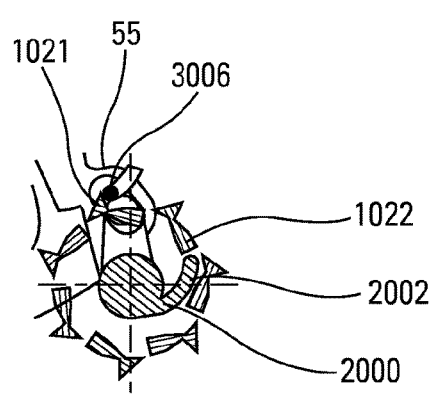

When the user inhales, the movable support means 50 are moved relative to the body 10 and thus relative to the support plate 3000, in the direction of arrow A in FIG. 15. The control opening 55 of said movable support means 50 thus drives the rigid finger 2001 of the actuator member 2000, and this causes the actuator member 2000 to turn in the direction of arrow B in FIG. 15, which is the first turning direction. The flexible tab 2002 of the actuator member 2000 slides over a tooth of the second set of teeth 1022, deforming, until it snap-fastens behind the next tooth of said second set of teeth 1022, as can be seen in FIG. 16. During this time, the lug 3006 of the support plate 3000 prevents the drum from turning at all in the direction of arrow B by co-operating with a tooth of the first set of teeth 1021 of the drum 1000. Thus, during inhalation, the actuator member 2000 turns in said first turning direction, but said drum 1000 remains stationary, blocked by the lug 3006 forming non-return means.

Figure 17:
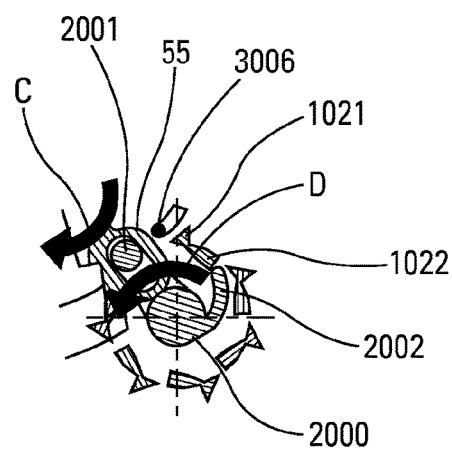

When the movable support means 50 are returned towards their initial position, after inhalation, the control opening 55 thus pivots in the opposite direction, in the direction of arrow C in FIG. 17, and drives the rigid finger 2001 of the actuator member 2000. This causes the actuator member 2000 to turn in the direction of arrow D, which is the second turning direction, opposite to the first turning direction. During this turning, the flexible tab 2002 pushes on a tooth of the second set of teeth 1022 of the drum, thus causing said drum 1000 to turn, likewise in the direction of arrow D. This rolls the blister strip 100 around said drum 1000. During this turning of the drum 1000, the deformable tab 3007 deforms and the lug 3006 of the support plate 3000 can slide over a tooth of the first set of teeth 1021, so as to snap-fasten behind the next tooth of said first set of teeth 1021.

The device is thus ready for another actuation cycle.

The present invention thus makes it possible to ensure that the used portion of the blister strip is rolled up reliably, said rolling taking place while the movable support means 50 are returning towards their non-dispensing position, after inhalation. This guarantees reliable rolling up of the strip, and thus reliable operation of the inhaler device.

The present invention therefore makes it possible to provide a dry-powder inhaler that provides one or more of the following features:

- a plurality of individual doses of powder stored in individual sealed blisters, e.g. 30 or 60 doses stored on a rolled-up strip;
- the powder is released by perforation that is achieved by the user inhaling, the blister being perforated by means of an inhalation detector system that is coupled to a prestressed release system;
- appropriately-shaped drive means that are engaged with blisters so as to move the blister strip after each inhalation, and bring a new full blister into a position in which it is to be opened by appropriate opening means;
- means for avoiding doses being lost in the event of the inhaler being opened, but in the absence of any inhalation;
- means for ensuring reliable rolling up of the blister-strip portion including the empty blisters;
- a dose indicator adapted to count the doses only in the event of inhalation.

Other features are also provided by the device of the invention as described above.

It should be observed that the various features, even if they are shown as being provided simultaneously on the inhaler, could be implemented separately. In particular, the inhalation trigger mechanism could be used regardless of the type of reservoir opening means, regardless of the use of a dose indicator, regardless of the way in which the individual blisters are arranged relative to one another, etc. The cocking means and the inhalation trigger system could be made in some other way. The same applies for other component parts of the device.

Various modifications are also possible for the skilled person without departing from the scope of the present invention as defined in the accompanying claims. In particular, the various characteristics and functions of the device described with reference to the drawings can be combined together in any appropriate manner.

The invention claimed is:

1. A fluid dispenser device including a body and at least one cover element that is mounted to pivot on said body between a closed position and an open position, said fluid dispenser device including a plurality of individual reservoirs each containing a single dose of fluid, said plurality of individual reservoirs being arranged on an elongate strip, opening means being provided for opening an individual reservoir each time the fluid dispenser device is actuated, said fluid dispenser device including movable support means that are adapted to move an individual reservoir against said opening means on each actuation, said movable support means being movable between a non-dispensing position and a dispensing position, the fluid dispenser device comprising a strip-rolling system comprising a drum and an actuator member, a leading end of said elongate strip being fastened to said drum, and said actuator member configured to turn relative to the body in a first turning direction when said movable support means are moved from their non-dispensing position towards their dispensing position, and in a second turning direction, opposite to said first turning direction, when said movable support means are moved from their dispensing position towards their non-dispensing position, said actuator member configured to cause said drum to turn only when turning in said second turning direction;

wherein said drum is prevented from turning in said first turning direction by a non-return mechanism comprising a lug arranged on a deformable tab, said lug co-operating with a first set of teeth of said drum so as to prevent said drum from turning in said first turning direction, said deformable tab configured to deform so as to enable said drum to turn in said second turning direction.

2. The fluid dispenser device according to claim 1, wherein said actuator member includes a flexible tab, said flexible tab configured to co-operate with a second set of teeth of said drum so as to turn said drum in said second turning direction, said flexible tab configured to deform so as to enable said actuator member to turn relative to said drum in said first turning direction.

3. The fluid dispenser device according to claim 1, wherein said actuator member includes a rigid finger that co-operates with a control opening in said movable support means.

4. The fluid dispenser device according to claim 1, including an inhalation trigger system that comprises a deformable air chamber that co-operates with an inhalation piece, and a trigger element that co-operates with said deformable air chamber, such that during inhalation through said inhalation piece, said deformable air chamber is deformed and said trigger element causes a reservoir to be opened by said opening means during inhalation through the inhalation piece.

5. The fluid dispenser device according to claim 1, wherein said opening means include a perforator element that is stationary relative to said main body and that is adapted to cut a closure wall of a reservoir in such a manner that the cut portion does not obstruct an opening of the reservoir formed by the opening means.

6. The fluid dispenser device according to claim 1, wherein the dose of fluid is a dose of powder.

7. A fluid dispenser device including a body and at least one cover element that is mounted to pivot on said body between a closed position and an open position, said fluid dispenser device including a plurality of individual reservoirs each containing a single dose of fluid, said plurality of individual reservoirs being arranged on an elongate strip, opening means being provided for opening an individual reservoir each time the fluid dispenser device is actuated, said fluid dispenser device including movable support means that are adapted to move an individual reservoir against said opening means on each actuation, said movable support means being movable between a non-dispensing position and a dispensing position, the fluid dispenser device comprising a strip-rolling system comprising a drum and an actuator member, a leading end of said elongate strip being fastened to said drum, and said actuator member configured to turn relative to the body in a first turning direction when said movable support means are moved from their non-dispensing position towards their dispensing position, and in a second turning direction, opposite to said first turning direction, when said movable support means are moved from their dispensing position towards their non-dispensing position, said actuator member configured to cause said drum to turn only when turning in said second turning direction;

wherein said actuator member includes a flexible tab, said flexible tab configured to co-operate with a set of teeth of said drum so as to turn said drum in said second turning direction, said flexible tab configured to deform so as to enable said actuator member to turn relative to said drum in said first turning direction.

8. The fluid dispenser device according to claim 7, wherein said drum is prevented from turning in said first turning direction by non-return means.

9. The fluid dispenser device according to claim 8, wherein said non-return means comprises a lug arranged on a deformable tab, said lug co-operating with a first set of teeth of said drum so as to prevent said drum from turning in said first turning direction, said deformable tab configured to deform so as to enable said drum to turn in said second turning direction.

10. The fluid dispenser device according to claim 7, wherein said actuator member includes a rigid finger that co-operates with a control opening in said movable support means.

11. The fluid dispenser device according to claim 7, including an inhalation trigger system that comprises a deformable air chamber that co-operates with an inhalation piece, and a trigger element that co-operates with said deformable air chamber, such that during inhalation through said inhalation piece, said deformable air chamber is deformed and said trigger element causes a reservoir to be opened by said opening means during inhalation through the inhalation piece.

12. The fluid dispenser device according to claim 7, wherein said opening means include a perforator element that is stationary relative to said main body and that is adapted to cut a closure wall of a reservoir in such a manner that the cut portion does not obstruct an opening of the reservoir formed by the opening means.

13. The fluid dispenser device according to claim 7, wherein the dose of fluid is a dose of powder.

* * * * *